United States Patent
Zobeck et al.

(10) Patent No.: US 10,633,651 B2
(45) Date of Patent: Apr. 28, 2020

(54) ASSAY METHODS AND COMPOSITIONS FOR DETECTING CONTAMINATION OF NUCLEIC ACID IDENTIFIERS

(71) Applicant: Agilent Technologies, Inc., Santa Clara, CA (US)

(72) Inventors: Katie Leigh Zobeck, Campbell, CA (US); Paige Anderson, Mountain View, CA (US); Javelin Chi, Sunnyvale, CA (US); Henrik Johansson, Stockholm (SE)

(73) Assignee: AGILENT TECHNOLOGIES, INC., Santa Clara, CA (US)

(*) Notice: Subject to any disclaimer, the term of this patent is extended or adjusted under 35 U.S.C. 154(b) by 0 days.

(21) Appl. No.: 15/645,085

(22) Filed: Jul. 10, 2017

(65) Prior Publication Data

US 2019/0010488 A1    Jan. 10, 2019

(51) Int. Cl.
| | | |
|---|---|---|
| *C12N 15/10* | (2006.01) | |
| *C12Q 1/68* | (2018.01) | |
| *C12Q 1/6848* | (2018.01) | |
| *C12Q 1/6874* | (2018.01) | |
| *C12Q 1/6806* | (2018.01) | |
| *C12Q 1/689* | (2018.01) | |

(52) U.S. Cl.
CPC ....... *C12N 15/1065* (2013.01); *C12Q 1/6806* (2013.01); *C12Q 1/689* (2013.01); *C12Q 1/6848* (2013.01); *C12Q 1/6874* (2013.01)

(58) Field of Classification Search
None
See application file for complete search history.

(56) References Cited

U.S. PATENT DOCUMENTS

| | | |
|---|---|---|
| 2013/0137587 A1 | 5/2013 | Van et al. |
| 2014/0378349 A1* | 12/2014 | Hindson .............. C12Q 1/6806 506/26 |
| 2015/0111789 A1 | 4/2015 | Betts et al. |
| 2015/0284712 A1 | 10/2015 | Kurihara et al. |
| 2016/0258006 A1 | 9/2016 | Van Eijk et al. |
| 2016/0265039 A1 | 9/2016 | Huang |

OTHER PUBLICATIONS

Kircher et al.( Nucleic acids research40.1 (2011):8 pages). (Year: 2011).*
Kircher 2011 supp (Year: 2011).*
HaloPlex HS Target Enrichment System for Illumina Sequencing Protocol, Dec. 2016, Version C1, Agilent Technologies, Inc., Santa Clara, CA.
HaloPlex Target Enrichment System for Illumina Sequencing Protocol, Jul. 2015, Version F1, Agilent Technologies, Inc., Santa Clara, CA.
SureSelect XT Target Enrichment System for Illumina Paired-End Multiplexed Sequencing Library Protocol, Jul. 2017, Version C1, Agilent Technologies, Inc, Santa Clara, CA.
SureSelect QXT Target Enrichment for Illumina Multiplexed Sequencing Protocol, Dec. 2016, Version D1, Agilent Technologies, Inc., Santa Clara, CA.
International Search Report and Written Opinion dated Aug. 29, 2018, Application No. PCT/US2018/032012, 17 pages.

* cited by examiner

*Primary Examiner* — Tracy Vivlemore
*Assistant Examiner* — Sahana S Kaup (57) ABSTRACT

The present invention relates to nucleic acid samples for massively parallel sequencing. More particularly, the present invention relates to assay methods, compositions and kits for detecting contamination of nucleic acid identifiers such as sample barcodes.

18 Claims, 9 Drawing Sheets

Specification includes a Sequence Listing.

AATGATACGGGCGACCACCGAACACTCTTTCCCTACACGACGCTCTTCCGATCTAACCATTGGAGATCGGAAG
AGCACACGT

Version 1

AATGATACGGGCGACCACCGAGATCTACACGCTGACGTCGAGACTTGTGATCAAGAGACAGAACTAGCTGAG
ATCGGAAGAGCACACGT

Version 2

|   | 1 | 2 | 3 | 4 | 5 | 6 | 7 | 8 | 9 | 10 | 11 | 12 |
|---|---|---|---|---|---|---|---|---|---|---|---|---|
| A | SBC1<br>QCBC1 | SBC9<br>QCBC9 | SBC17<br>QCBC17 | SBC25<br>QCBC25 | SBC33<br>QCBC33 | SBC41<br>QCBC41 | SBC49<br>QCBC1 | SBC57<br>QCBC9 | SBC65<br>QCBC17 | SBC73<br>QCBC25 | SBC81<br>QCBC33 | SBC89<br>QCBC41 |
| B | SBC2<br>QCBC2 | SBC10<br>QCBC10 | SBC18<br>QCBC18 | SBC26<br>QCBC26 | SBC34<br>QCBC34 | SBC42<br>QCBC42 | SBC50<br>QCBC2 | SBC58<br>QCBC10 | SBC66<br>QCBC18 | SBC74<br>QCBC26 | SBC82<br>QCBC34 | SBC90<br>QCBC42 |
| C | SBC3<br>QCBC3 | SBC11<br>QCBC11 | SBC19<br>QCBC19 | SBC27<br>QCBC27 | SBC35<br>QCBC35 | SBC43<br>QCBC43 | SBC51<br>QCBC3 | SBC59<br>QCBC11 | SBC67<br>QCBC19 | SBC75<br>QCBC27 | SBC83<br>QCBC35 | SBC91<br>QCBC43 |
| D | SBC4<br>QCBC4 | SBC12<br>QCBC12 | SBC20<br>QCBC20 | SBC28<br>QCBC28 | SBC36<br>QCBC36 | SBC44<br>QCBC44 | SBC52<br>QCBC4 | SBC60<br>QCBC12 | SBC68<br>QCBC20 | SBC76<br>QCBC28 | SBC84<br>QCBC36 | SBC92<br>QCBC44 |
| E | SBC5<br>QCBC5 | SBC13<br>QCBC13 | SBC21<br>QCBC21 | SBC29<br>QCBC29 | SBC37<br>QCBC37 | SBC45<br>QCBC45 | SBC53<br>QCBC5 | SBC61<br>QCBC13 | SBC69<br>QCBC21 | SBC77<br>QCBC29 | SBC85<br>QCBC37 | SBC93<br>QCBC45 |
| F | SBC6<br>QCBC6 | SBC14<br>QCBC14 | SBC22<br>QCBC22 | SBC30<br>QCBC30 | SBC38<br>QCBC38 | SBC46<br>QCBC46 | SBC54<br>QCBC6 | SBC62<br>QCBC14 | SBC70<br>QCBC22 | SBC78<br>QCBC30 | SBC86<br>QCBC38 | SBC94<br>QCBC46 |
| G | SBC7<br>QCBC7 | SBC15<br>QCBC15 | SBC23<br>QCBC23 | SBC31<br>QCBC31 | SBC39<br>QCBC39 | SBC47<br>QCBC47 | SBC55<br>QCBC7 | SBC63<br>QCBC15 | SBC71<br>QCBC23 | SBC79<br>QCBC31 | SBC87<br>QCBC39 | SBC95<br>QCBC47 |
| H | SBC8<br>QCBC8 | SBC16<br>QCBC16 | SBC24<br>QCBC24 | SBC32<br>QCBC32 | SBC40<br>QCBC40 | SBC48<br>QCBC48 | SBC56<br>QCBC8 | SBC64<br>QCBC16 | SBC72<br>QCBC24 | SBC80<br>QCBC32 | SBC88<br>QCBC40 | SBC96<br>QCBC48 |

FIG. 7

ASSAY METHODS AND COMPOSITIONS FOR DETECTING CONTAMINATION OF NUCLEIC ACID IDENTIFIERS

CROSS REFERENCE TO RELATED APPLICATIONS

None.

FIELD OF THE INVENTION

The present invention relates to the field of molecular biology. In particular, the present invention relates to assay methods and compositions for detecting contamination of nucleic acid identifiers such as sample barcodes.

BACKGROUND OF THE INVENTION

Identifiers (e.g., sample barcodes or molecular barcodes) can be present in nucleic acids for a variety of purposes. Most commonly, sample barcodes are added to target nucleic acid molecules prior to the amplification and/or sequencing of such molecules, so that the origin or source of sequence information can be identified. Nucleic acid molecules from different samples can be pooled together and subjected to massively parallel sequencing in order to efficiently determine sequence information from numerous different samples. Prior to sequencing, sample identifiers (often referred to as sample barcodes) can be added to the nucleic acid molecules, and this facilitates grouping, analysis, and interpretation of information. As another example, molecular barcodes can be added to target nucleic acid molecules prior to amplification, so that the replicates of the initial target molecule can subsequently be identified and grouped together.

Sample barcodes are frequently used with target molecules that will be analyzed by massively parallel sequencing, so that nucleic acid molecules from different samples can be pooled for sequencing, and the sequence information can be assigned to a sample. Scientists and laboratories that perform massively parallel sequencing occasionally detect a sample barcode in a pool even when this sample barcode was not included in the sequencing pool. This indicates that a contaminating sample barcode is present in the pooled nucleic acids, which may be caused by a sample barcode aliquot containing more than one sample barcode sequence, namely the expected barcode sequence and the contaminating barcode sequence. Contaminating barcodes could be introduced at any stage of the preparation of sample barcode aliquots, beginning from the earliest stage, including the synthesis and purification of DNA oligos, or though handling steps in the process of diluting and aliquoting sample barcode sequences. Even when present at low frequencies, such as 1% or lower, the presence of contaminating sample barcodes can create problems with regard to the reliability and interpretation of the sequence information.

Sample barcodes are often provided in a set of containers, such as a well plate, where each container holds a different sample barcode. When the sample barcodes are used in laboratory analysis, such as by pipetting the sample barcodes from their containers to the various samples to be analyzed, there is a risk that a container or sample may become contaminated.

Contamination of sample barcodes could be detected by preparing individual sequencing libraries for each sample barcode and sequencing them individually. Alternatively contamination could be detected with a pooling scheme that provides the ability to compare a sample barcode and contamination of another sample barcode in at least one of the pools. However, a large number of pools would have to be prepared and sequenced in separate sequencing runs in order to isolate sample barcodes from a large number of samples, such as 48 or 96 samples. This would be expensive, inefficient and time-consuming. It also has the potential of erroneously finding contamination in a sample barcode that was not present in the tube, but instead introduced in one of the many library preparation steps, leading to false positives.

SUMMARY OF THE INVENTION

As one aspect of the present invention, methods are provided for attaching assay identifiers (e.g., quality control barcodes) to a set of oligonucleotide samples comprising oligonucleotides, where each oligonucleotide comprises a 5' constant region, a sample identifier (e.g., a sample barcode), and a 3' constant region, and each sample identifier is unique in the set in the absence of contamination. In some embodiments, the constant regions comprise standard amplification regions for a sequencing platform, or their reverse complement. For example, in some embodiments, the 5' constant region is an Illumina Index 1 sequence and the 3' constant region is the reverse complement of Illumina P7 sequence (P7'), and in other embodiments, the orientation is reversed such that the 5' constant region is an Illumina P7 sequence and the 3' constant region is an Illumina Read 2 sequence. The methods comprise providing each of the oligonucleotide samples of the set in a separate vessel, so that each vessel comprises only one sample identifier unless one or more of the samples is contaminated. The methods also comprise amplifying the oligonucleotides with an assay primer and a second primer in each vessel. Assay primers comprise one or more constant regions (such as P5 and a Read 1 Primer sequence), an assay identifier, and a priming portion that is the same as or complementary to one of the constant regions of the oligonucleotides. Each vessel comprises only one assay identifier unless one or more of the assay primers are contaminated. The method thus provides oligonucleotide amplicons comprising an assay identifier and a sample identifier.

As another aspect, methods are provided for detecting contamination in a set of oligonucleotides comprising sample identifiers. The methods comprise providing a set of oligonucleotide samples comprising oligonucleotides, each oligonucleotide having a 5' constant region, a sample identifier (such as a sample barcode), and a 3' constant region. Oligonucleotides within a sample have the same sample identifier and each of the samples within the set has a different sample identifier, unless one or more of the samples is contaminated. The methods also comprise amplifying the oligonucleotides or complements of the oligonucleotides with assay primers and a second primer. A different assay primer is used for each sample, and each assay primer comprises a priming portion and an assay identifier (such as a QC barcode), thereby generating a set of oligonucleotide amplicons. Each oligonucleotide amplicon comprising one of the assay identifiers, the 5' constant region, one of the sample identifiers, and the 3' constant region. The methods also comprise pooling the oligonucleotide amplicons in one or more pools; sequencing the one or more pools to determine sequence information for at least the sample identifier and the assay identifier of the oligonucleotide amplicons; determining whether the sample identifiers in a first pool include a contaminating sample identifier; and determining whether the assay identifiers in the first pool include a contaminating assay identifier.

In some embodiments, the present methods comprise pooling the oligonucleotide amplicons in at least two pools, and separately sequencing the first pool and the second pool to determine sequences for at least the sample identifier and the assay identifier of the oligonucleotide amplicons. The present methods can also comprise determining whether the sample identifiers in the second pool include a contaminating sample identifier. In some embodiments, the present methods also comprise determining whether the assay identifiers in the second pool include a contaminating assay identifier. In some embodiments, the present methods further comprise identifying a contaminating sample identifier in a first pool by determining that the contaminating sample identifier is from a second pool. In some embodiments, the present methods further comprise identifying a contaminating sample identifier in a first pool by determining that the second pool does not include a contaminating assay identifier. In some embodiments, the present methods further comprise identifying a contaminating assay identifier in a first pool by determining that the second pool includes a contaminating assay identifier. In some embodiments, the contaminating sample identifier is determined by one or both of (i) identifying one or more of the sample identifiers that are associated with more than one assay identifier, and (ii) identifying assay identifiers that are associated with more than one sample identifier As another aspect, compositions are provided which are useful in assays adapted for determining contamination in a set of oligonucleotides comprising sample identifiers. The compositions comprise at least one oligonucleotide having a 5' constant region, a sample identifier (such as a sample barcode), and a 3' constant region, and at least one assay primer comprising a priming portion and an assay identifier. In some embodiments, the compositions further comprise one or more of a DNA polymerase, and deoxynucleotides.

As yet another aspect, kits are provided for assays adapted for determining contamination in a set of oligonucleotides comprising sample identifiers. The kits comprise at least 8 assay primers, alternatively at least 16 assay primers, alternatively at least 32 assay primers, alternatively at least 48 primers or at least 96 primers, in separate vessels. Each assay primer identifier comprises a priming portion and an assay identifier.

In some embodiments of the foregoing aspects, a set or pool of oligonucleotide samples comprises at least 8 samples, alternatively at least 16 samples, alternatively at least 32 samples, alternatively at least 48 samples, alternatively at least 96 samples, where each sample has a sample identifier that is unique within the set or pool. In some embodiments, a set of assay primers comprises at least 32 assay identifiers, alternatively at least 48 assay identifiers, alternatively at least 96 assay identifiers, where each assay primer has an assay sample identifier that is unique within the set or pool.

DETAILED DESCRIPTION OF THE INVENTION

The present methods, compositions and kits are useful for detecting contamination in a set of oligonucleotides for nucleic acid samples and allow the production of sample identifier sets that are substantially free of contamination. This is a significant advance and benefit, as the presence of sample barcode contamination may result in result in false calling of genetic variants which can have severe consequences for research and clinical applications.

The methods, compositions and kit employ oligonucleotides which have a 5' constant region, a sample identifier, and a 3' constant region. Each of the oligonucleotides within a sample has the same sample identifier and each of the samples within the set has different sample identifiers, unless one or more of the samples is contaminated by a contaminating sample identifier. In some embodiments, each of the samples within the set has a sample identifier which is unique in the set, meaning that it is intended to be and will be unique in the absence of contamination.

A "sample identifier" comprises a sample barcode or any degenerate or random sequence that can be used to identify a sample. Sample identifiers may be flanked (directly or indirectly) by constant regions. In some embodiments, the sample identifier can be a sample barcode comprising 6 or more random or degenerate nucleotides; alternatively the sample identifier can be a sample barcode comprising 8 or more random or degenerate nucleotides, or 10 or more random or degenerate nucleotides. In some embodiments, a sample identifier comprises 8 known bases, and an assay identifier comprises 10 degenerate bases. In other embodiments, a sample identifier comprises 4 known bases or 6 known bases. In some embodiments, the number of bases in the sample identifier can be selected based on the number of samples to be distinguished. Longer sample identifiers and sample barcodes are also possible. For example, a sample identifier comprising 18 bases (8 known bases and 10 degenerate bases) has been employed to prepare a library of oligonucleotides for an Ion Torrent sequencing platform. A sample identifier with more than 19 bases is also feasible and may be desired, especially if the assay is used for other sequencing platforms and applications. In some embodiments, the complement of an initial sample barcode is in an oligonucleotide amplicon, and this complement is also considered a sample identifier.

A "constant" region is one that comprises a known sequence, and because it is known, it can serve a desired function. A constant region will generally be the same or substantially the same among oligonucleotides of a set. The known sequence can serve as a priming site (region) for amplification or primer extension, and/or can hybridize to a nucleic acid attached to a support. In some embodiments, a constant region comprises a sequence of standard region, such as a standard amplification region used in a sequencing platform. A constant region can comprise a number of nucleotides from a known or standard region sufficient for the function of the standard region, such as a sufficient number of nucleotides to hybridize to a standard primer for amplification.

A "contaminating" molecule or sequence is one that is not designed to be in a set or pool, or should not be present in a set or pool or sample unless there is some contamination. For example, a barcode in a first set or pool of sequences is a contaminating barcode if it should not be present in the first set or pool and/or should only be present in a second set or pool.

The present methods and compositions provide a solution to the problem of identifying contamination in sets of oligonucleotides comprising sample identifiers such as sample barcodes. The present techniques have a relatively small number of handling steps, which is desirable since handling steps increase risk of contamination. Additionally, a pooling scheme and analysis method is provided which reduces the number of pools and sequencing runs required to detect contamination between samples. Instead of a large number of pools, this present method can reduce the pools used to detect contamination in a set of 96 sample identifiers. In some embodiments, two sequencing pools are used to detect sample identifier contamination in a set of 96 sample identifiers.

The present methods and compositions can also be used to amplify oligonucleotides (such as library molecules, adaptors, aptamers or other ssDNA molecules used to target proteins or peptides) which have a series of random nucleotides (which are considered sample identifiers herein) between two constant regions in order to detect sequence diversity, including detection of molecular barcodes. It could also be used to identify single nucleotide polymorphs (SNPs) or sites of mutagenesis in known regions of DNA.

The oligonucleotides which may be assayed by the present methods include adaptors for nucleic acid molecules or regions from standard adaptors, such as the amplification region from a standard adaptor for a sequencing platform. The oligonucleotide can also include a label, tag, or other moiety. By way of example, the oligonucleotide includes a biotin moiety, allowing for enrichment of the oligonucleotides by binding to avidin or steptavidin. This approach is used in the commercially available Haloplex kit (Agilent Technologies). The oligonucleotides which may be assayed by the present methods include library molecules, which are molecules prepared to be part of a library for a sequencing platform. A library molecule generally comprises an insert to which a sample identifier and one or more standard regions for sequencing platforms are attached. Other regions can also be included in a library molecule. With a library molecule, the sample identifier can be a molecular barcode, or it can be a second sample barcode that is in addition to a first sample barcode.

The methods also comprise amplifying the oligonucleotides or complements of the oligonucleotides with assay primers and a second primer. A different assay primer is used for each sample, and each assay primer comprises a priming portion and an assay identifier (such as a QC barcode), thereby generating a set of oligonucleotide amplicons. Each oligonucleotide amplicon comprises one of the assay identifiers, the 5' constant region, one of the sample identifiers, and the 3' constant region. The present assay methods can be readily adapted to various standardized sequencing platforms (for example, the Illumina and Ion Torrent sequencing platforms), by selecting constant regions that are standard for those platforms.

In some embodiments, the present methods detect sample identifier contamination at a level less than 1%, alternatively less than 0.5%, alternatively less than 0.1% using a small number of handling steps to avoid or prevent assay-induced contamination, and provide a method of pooling and analysis, such that a small number of sequencing runs is performed. The present disclosure provides a fast and relatively inexpensive method to prepare libraries from potentially contaminated oligonucleotides having sample identifiers. The libraries are adapted for sequencing, especially massively parallel sequencing, on one or more desired sequencing platforms.

In some embodiments, the oligonucleotide amplicons comprise a 5' constant region and a 3' constant region. Furthermore, the 5' constant region comprises a standard 5' adaptor for a sequencing platform and a sequencing priming region, an assay identifier, a middle constant region comprising a sequencing priming region, and a sample identifier, and the 3' constant region comprising a standard 3' adaptor for a sequencing platform. In some embodiments, the oligonucleotide amplicons comprise (i) a 5' constant region comprising a standard 5' adaptor for a sequencing platform and a sequencing priming region, (ii) an assay identifier, (iii) a middle constant region comprising a sequencing priming region, (iv) a sample identifier, and (v) a 3' constant region of comprising a standard 3' adaptor for a sequencing platform. For example, a standard 5' adaptor can comprise an Illumina P5 or P5' sequence, and a standard 3' adapter can comprise an Illumina P7 or P7' sequence. P7' indicates the complement of P7; likewise, P5' indicates the complement of P5. In other embodiments, the oligonucleotide amplicon comprises a 5' constant region comprising a standard 5' adapter, a sample identifier, a middle constant region, an assay identifier, and a 3' constant region comprising a standard 3' adapter.

The present methods, compositions and kits can also be used to a modify an oligonucleotide comprising a region that is standard for a first sequencing platform (for example, an amplification region or a sequencing primer site (region)), so that it includes a region that is standard for a different sequencing platform. In some embodiments, a second primer comprises a 3' region complementary to a 3' constant region of the oligonucleotides, and the second primer further comprises a 5' region comprising a standard amplification region, wherein the 3' constant region of the oligonucleotides comprises a standard amplification region for a different sequencing platform than the standard amplification region of the 5' region of the second primer.

The present disclosure also provides novel pooling and sequencing schemes for identifying contamination of sample identifiers and assay identifiers. In some embodiments, the present methods comprise pooling the oligonucleotide amplicons in at least two pools; sequencing the two pools to determine the sequences of at least portions of the oligonucleotide amplicons comprising the sample identifiers and the assay identifiers; determining whether the sample identifiers in the second pool include a contaminating sample identifier; and determining whether the assay identifiers in the second pool include a contaminating assay identifier. In some embodiments, the present methods further comprise determining a contaminating sample identifier by determining that the contaminating sample identifier is from a second pool. In some embodiments, the methods further comprise identifying a contaminating sample identifier by determining that the second pool does not include a contaminating assay identifier. In some embodiments, the present methods further comprise identifying a contaminating assay identifier by determining that the second pool does not include a contaminating assay identifier.

In some embodiments, the present methods further comprise grouping sequences of the oligonucleotide amplicons according to the assay identifiers to form assay groups; and determining if there is more than one sample identifier sequence in each of the assay groups. In some embodiments, the present methods further comprise grouping sequences of the oligonucleotide amplicons according to the sample identifiers to form sample groups; and determining if there is more than one assay identifier sequence in each of the sample groups. In some embodiments, the methods comprise forming at least two pools from the oligonucleotide amplicons; sequencing at least two pools of amplicons to obtain sequence information of the oligonucleotide amplicons; wherein the sequence information for the individual oligonucleotide amplicon at least comprises the sequence of the assay identifier and the sample identifier. In some embodiments, the present methods can comprise grouping amplicon sequence information according to the assay identifier, and determining if grouped amplicon sequence information contains more than one of the sample identifiers.

The methods can comprise determining if there is a mismatch between an assay identifier and a sample identifier, such as where at least one of the sample identifiers is associated an assay identifier that it should not be associated with, and/or where at least one of assay identifiers is associated with a sample identifier that it should not be associated with.

The present methods can be used with sample preparation kits for NGS. They can also be used with library preparation reagents. The present methods can also be employed to assay target enrichment kits and sets that contain sample barcodes or other identifiers, including SureSelect reagent kits. SureSelect kits (available from Agilent Technologies) contain oligonucleotides having a sample identifier and having one or more constant regions 5' and 3' to the sample identifier, namely PCR primers.

The present disclosure allows for the production of sample identifier sets or kits that are substantially free of contamination, such as having less than 0.1% of a contaminating sample identifier, or less than 0.01%.

Figure 1A:
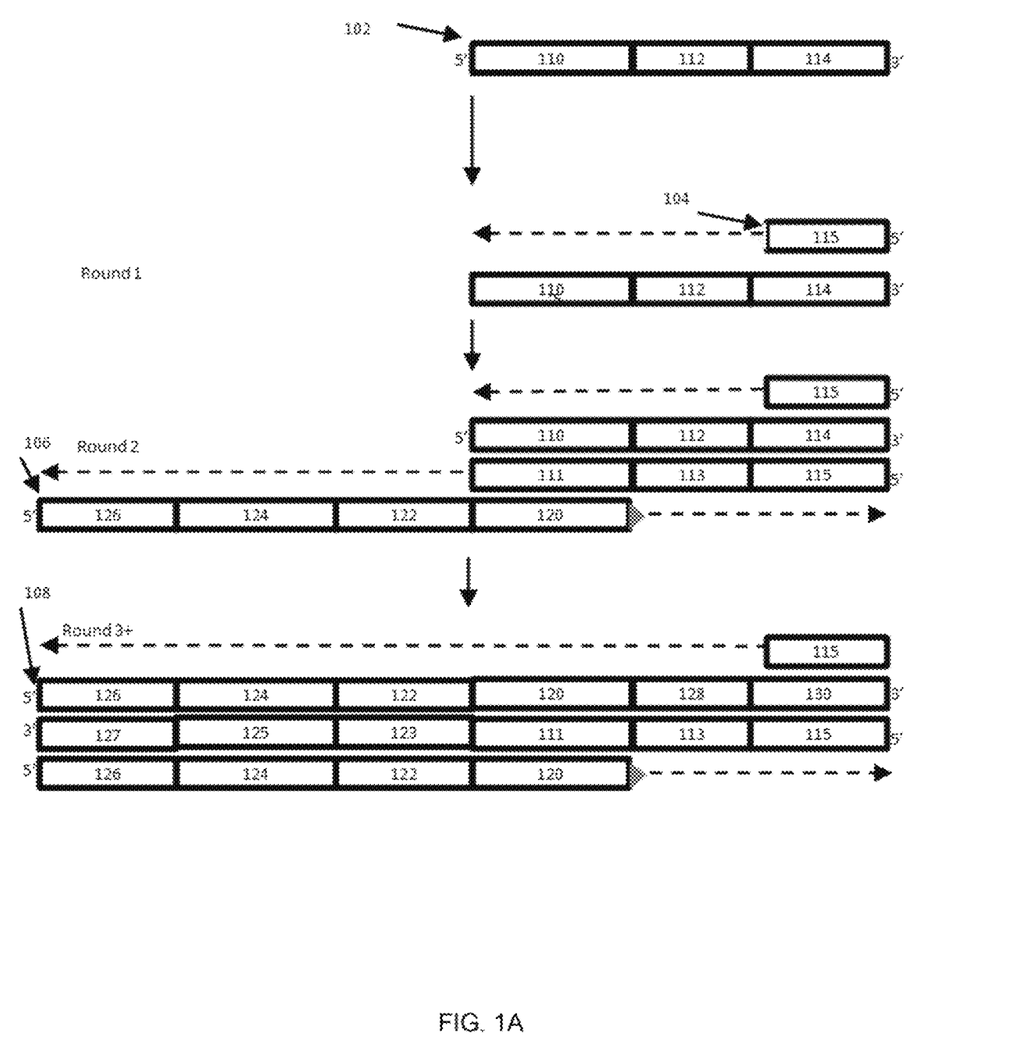
FIGS. 1A, 1B and 1C show embodiments of the present methods of attaching an assay identifier to an oligonucleotide having a sample identifier.

In FIG. 1A, an oligonucleotide 102 comprises a 5' constant region 110, a sample identifier 112, and a 3' constant region 114. For example, the 5' constant region 110 can comprise a standard sequence such as an Illumina Index 1 sequence, the sample identifier 112, and the 3' constant region 114 can comprise a standard amplification sequence, such as the Illumina P7' sequence. The constant regions can comprise any standard priming site (region) for amplification or sequencing. The oligonucleotide 102 is amplified using a primer 104 having a priming region 115 complementary to at least a portion of the 3' constant region 114. For example, the primer 104 can be a P7 primer. In the same step or a subsequent step, the oligonucleotide 102 or complement thereof is amplified with a primer 106 having a priming region 120 complementary to at least a portion of the 5' constant region 110 or its complement 111. The primer also comprises an assay identifier 122 and one or more constant regions 126, 124 (for example an Illumina P5 sequence 126 and a read 1 sequencing primer 124). Additional rounds of amplification produce oligonucleotide amplicons 108 comprising one or more constant regions 126, 124, the assay identifier 122, the sequence of the 5' constant region 120 of the initial oligonucleotide, the sample identifier sequence 128, and the 3' constant region 130 of the initial oligonucleotide. The sample identifier sequence 128 in the amplicons 108 is generally an identical copy of the sample identifier 112 of the oligonucleotide 102. Constant region 120 of the amplicon 108 will be mostly identical to constant region 110 of the oligonucleotide 102, however either could be partially truncated. For example, constant region 110 could be truncated on the 5' end, and constant region 120 could be truncated on the 3' end. Likewise, constant region 130 of the amplicon 108 and constant region 114 of the oligonucleotide 102 will generally be the same, though constant region 114 could be partially truncated on the 3' end, and constant region 130 could be partially truncated on the 5' end. The oligonucleotide amplicons 108 are adapted for sequencing on a standard platform for massively parallel sequencing due to the constant regions.

Figure 1B:
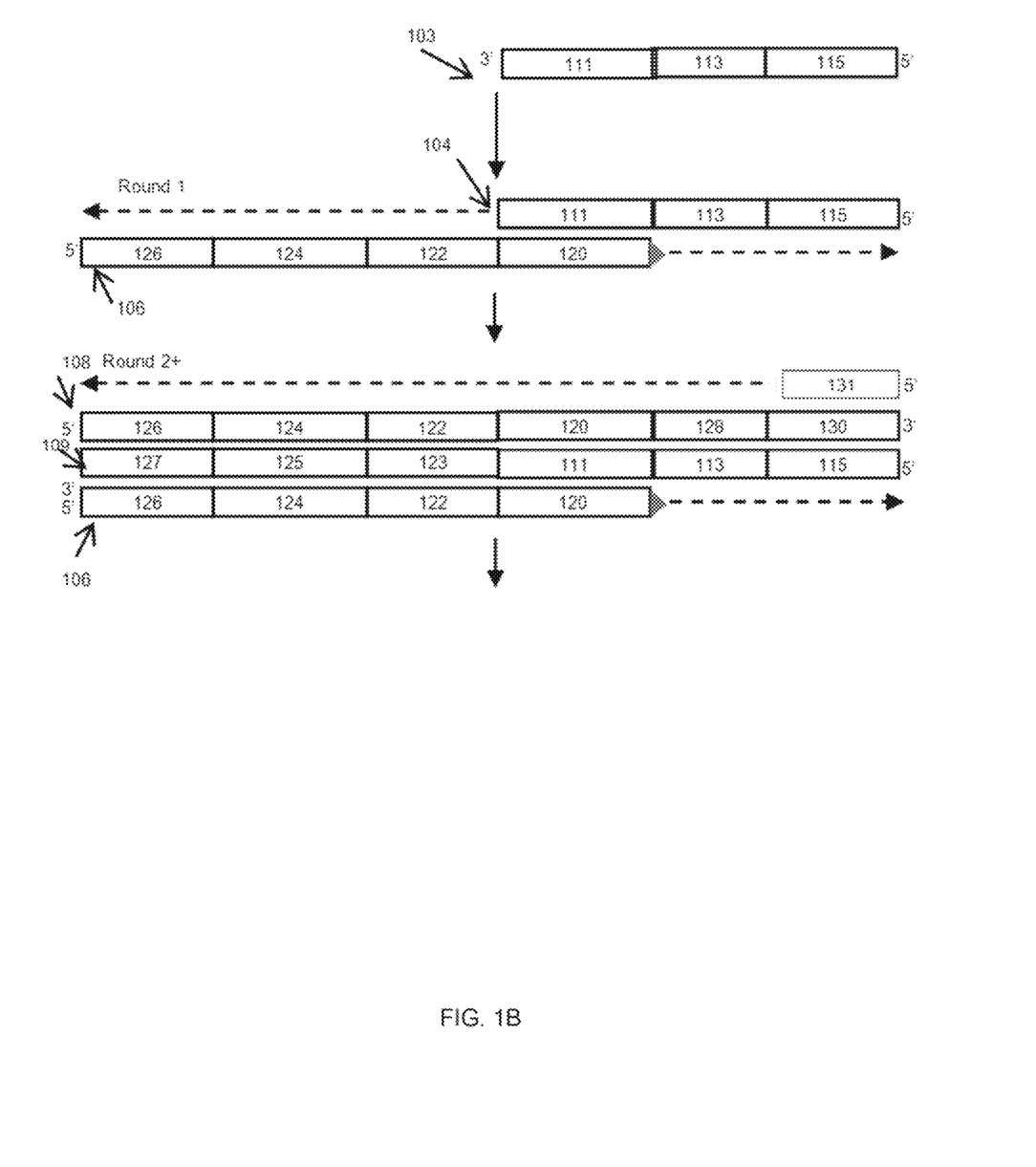

FIG. 1B shows another embodiment of the present methods. In this embodiment, oligonucleotide 103 comprises a 3' constant region 111, a sample identifier 113, and a 5' constant region 115. For example, the 3' constant region 111 can be the Illumina Read 2 sequence (or another standard region for a sequencing platform), and the 5' constant region 115 can be an Illumina P7 sequence or any standard priming site (a region) for amplification or sequencing. Amplification produces oligonucleotide amplicons 109 comprising one or more constant regions 127, 125, the assay identifier 123, the 3' constant region 111, the sample identifier sequence 113, and the sequence of the 5' constant region 115. Additional rounds of amplification can be conducted with primer 131 which has the same sequence as a portion of constant region 115 sufficient to function as a primer.

Figure 1C:
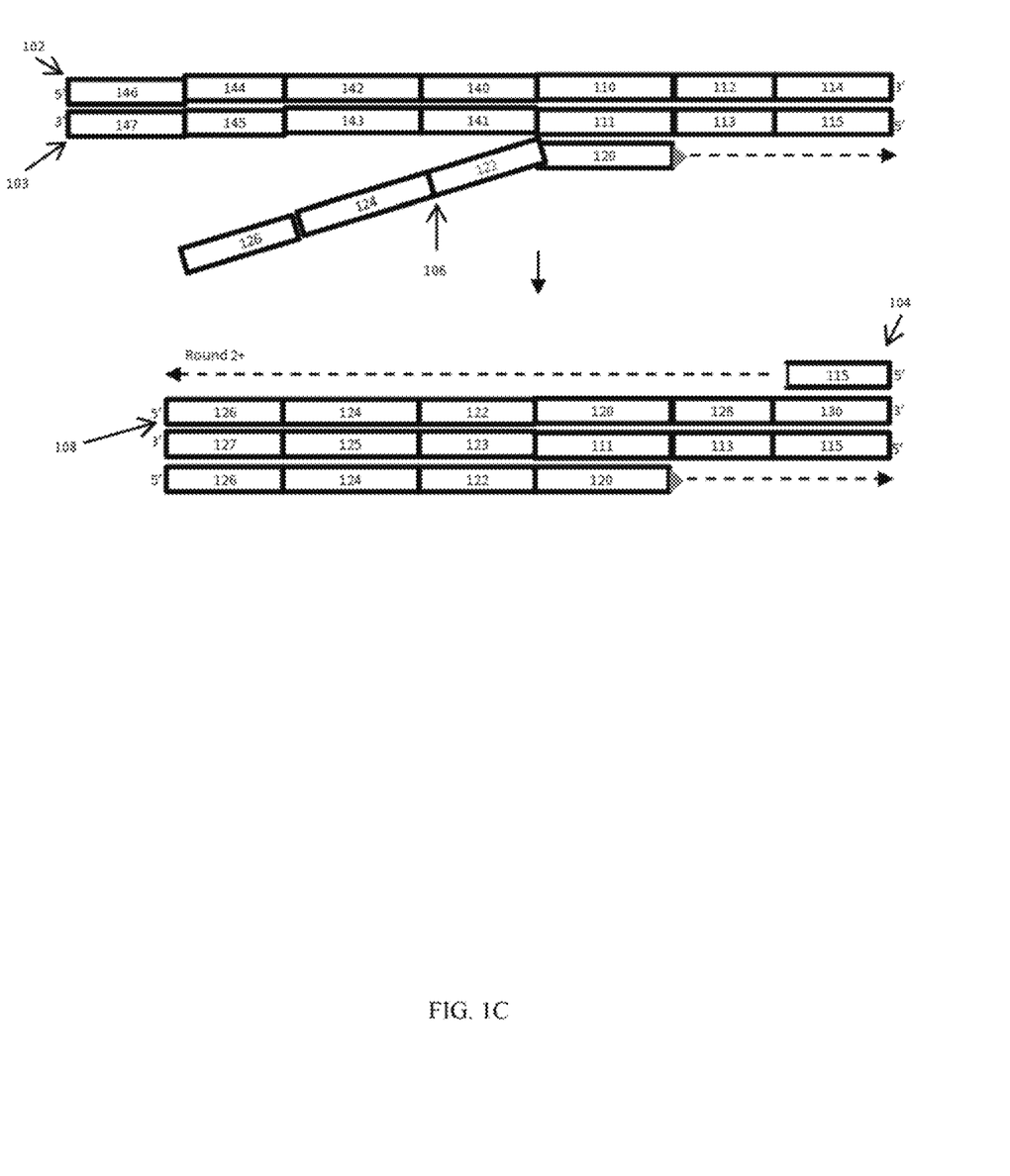

FIG. 1C demonstrates how the assay method can be performed when the initial oligonucleotide is a library molecule, that is a molecule comprising an insert to which a sample identifier and standard regions for sequencing platforms are attached. In this embodiment, the assay method can detect contamination that occurred during the library preparation. The oligonucleotide 102 comprises a first 5' constant region 110, a sample identifier 112, a 3' constant region 114, and further comprises an insert 140, a second 5' constant region, 142 (such as a Read 1 priming site), an optional second sample identifier 144, and a third 5' constant region 146 (for example, an amplification priming site). The insert 140 comprises a target sequence to be studied, analyzed or subjected to additional testing, such as sequencing on a massively parallel sequencing platform. A second sample identifier 144 is optionally included in many library preparations. Oligonucleotide 103 (which is a complementary strand of oligonucleotide 102) comprises a first 3' constant region 111, a sample identifier 113, a 5' constant region 115, and further comprises an insert 141, a second 3' constant region 143 (such as a Read 1 priming site), a optional second sample identifier 145, and a third 3' constant region 147 (for example, an amplification priming site). The oligonucleotide 102 is amplified using an assay primer 104 having a priming region 115 complementary to at least a portion of the 3' constant region 111. For example, the primer 104 can be a P7 primer. In the same step or a subsequent step, the oligonucleotide 102 or complement thereof is amplified with a primer 106 having a priming region 120 complementary to at least a portion of the 5' constant region 110 or its complement 111. The primer also comprises an assay identifier 122 and one or more constant regions 126, 124 (for example an Illumina P5 sequence 126 and a Read 1 sequencing primer region 124). Additional rounds of amplification produce oligonucleotide amplicons 108 comprising one or more constant regions 126, 124, the assay identifier 122, the sequence of the 5' constant region 120 of the initial oligonucleotide, the sample identifier sequence 128, and the 3' constant region 130 of the initial oligonucleotide. In the embodiment shown, oligonucleotide amplicon 108 does not include insert 140, but in some embodiments, primer 106 binds a region 3' to the insert 140, and the insert 140 is thereby included in the amplicons. A pooling method (as described in Example 4) can be employed on a library prepared with two or more sample barcodes (where the barcodes are attached via either ligation or amplification) and the pooling method can be used to identify if sample barcode contamination occurred after the library preparation was performed.

By the selection of constant regions and priming regions on the assay primers, this method is adaptable for different library preparation methods (including Haloplex XTHS, Haloplex HS, SureSelect XT, and SureSelect QXT, all from Agilent) and different standardized sequencing platforms (including Illumina and Ion Torrent). Sequencing platforms for massively parallel sequencing include Ion Torrent PGM and Proton semiconductor sequencers, and Illumina MiSeq, HiSeq, MiniSeq, and NextSeq. Other sequencing platforms are in development and the present compositions and methods can be used with the standard amplification regions for those platforms.

In some embodiments, constant regions on the oligonucleotide and/or the assay identifier comprise sequences suitable for use on a standardized sequencing platform. For example, a constant region can have the sequence of an amplification region for an lumina sequencing platform, such as an Illumina P5 sequence or an Illumina P7 sequence, or such as an Ion Torrent Adapter A sequence or an Ion Torrent Adapter P1 sequence, or such as the sequencing primer regions, such as Illuminna Read1, Index1, Read2 or Index2. Other amplification regions or sequencing primer regions can be used for different platforms. Table 1 sets forth the sequences of standard regions currently used in Illumina and Ion Torrent sequencing platforms:

TABLE 1

| Illumina | P5 | 5' | AATGATACGGCGACCACCGA 3' (SEQ ID NO: 1) |
|---|---|---|---|
| Illumina | P7 | 5' | CAAGCAGAAGACGGCATACGAGAT 3' (SEQ ID NO: 2) |
| Illumina | Read1 | 5' | ACACTCTTTCCCTACACGACGCTC 3' TTCCGATCT (SEQ ID NO: 3) |
| Illumina | Index1 | 5' | GATCGGAAGAGCACACGTCTGAAC 3' TCCAGTCAC (SEQ ID NO: 4) |
| Illumina | Read2 | 5' | GTGACTGGAGTTCAGACGTGTGCT 3' CTTCCGATCT (SEQ ID NO: 5) |
| Illumina | Index2 | 5' | AGATCGGAAGAGCGTCGTGTAGGG 3' AAAGAGTGT (SEQ ID NO: 6) |

TABLE 1-continued

| IonTorrent | A | 5' | CCATCTCATCCCTGCGTGTCTCCG 3' ACTCAG (SEQ ID NO: 7) |
|---|---|---|---|
| IonTorrent | P1 | 5' | CCTCTCTATGGGCAGTCGGTGAT 3' (SEQ ID NO: 8) |

In some embodiments, a constant region of an oligonucleotide con irises a sequence selected from the sequences set forth in Table 1.

Figure 5:
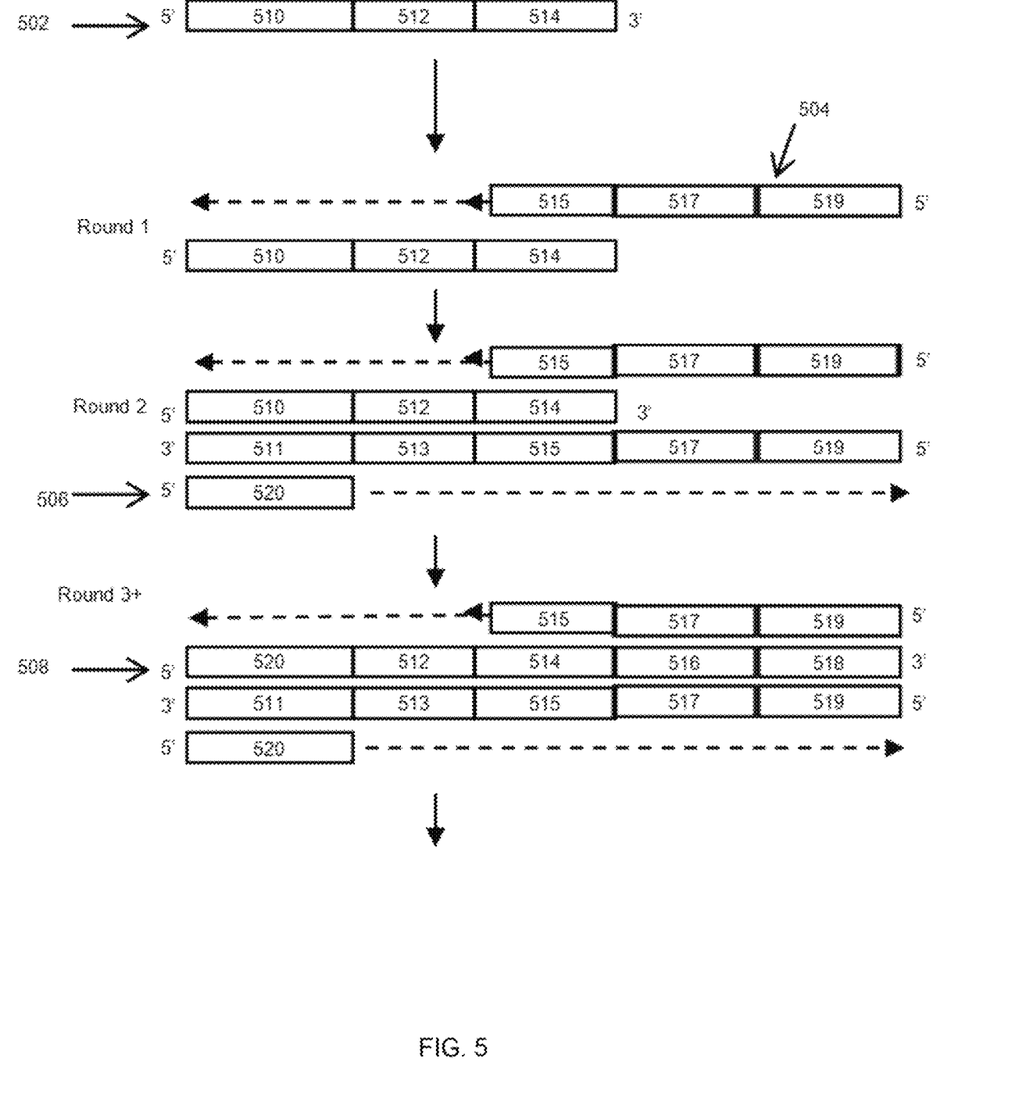
FIG. 5 shows another embodiment of the present methods of attaching an assay identifier to an oligonucleotide having a sample identifier, where the identifier is attached at a 3' location relative to the sample identifier.

FIG. 5 shows how the present methods and compositions can be used to add an assay identifier at a 3' location relative to the sample identifier. This approach is especially suitable for oligonucleotides which are adapters configured for attachment to 5' ends of target molecules to be sequenced or primers intended to amply the 5' end of target molecules. Thus, in this embodiment, the present methods are particularly suited for detecting identifiers present in a 5' adaptor (and is an alternative to a 3' adaptor as shown in FIG. 1).

In FIG. 5, an oligonucleotide 502 comprises a 5' constant region 510, a sample identifier 512, and a 3' constant region 514. For example, the 5' constant region 510 can be an Illumina P5 sequence, the sample identifier 512 can be a sample barcode, and the 3' constant region 514 can be an Illumina Read 1 sequence. The oligonucleotide 502 is amplified using a primer 504 having a priming region 515 complementary to at least a portion of the 3' constant region 514. For example, the priming region 515 can be the reverse complement of the 3' constant region 514, that is the reverse complement of an Illumina Read 1 sequence. Primer 504 also comprises an assay identifier 517 and an adapter 519 for a sequencing platform or its complement, for example the reverse complement of Illumina P7 (P7'). The oligonucleotide 502 or complement thereof is amplified with a primer 506 having a priming region 520 complementary to at least a portion of the 5' constant region 510 or its complement. Additional rounds of amplification produce oligonucleotide amplicons 508 comprising a 3' adapter 518, the assay identifier 522, 516, the 3' constant region 514, the sample identifier 512, and 5' constant region 520. The oligonucleotide amplicons 508 are adapted for sequencing on a standard platform for massively parallel sequencing because at least one, and often both, constant regions include an adapter for such a platform.

Figure 6:
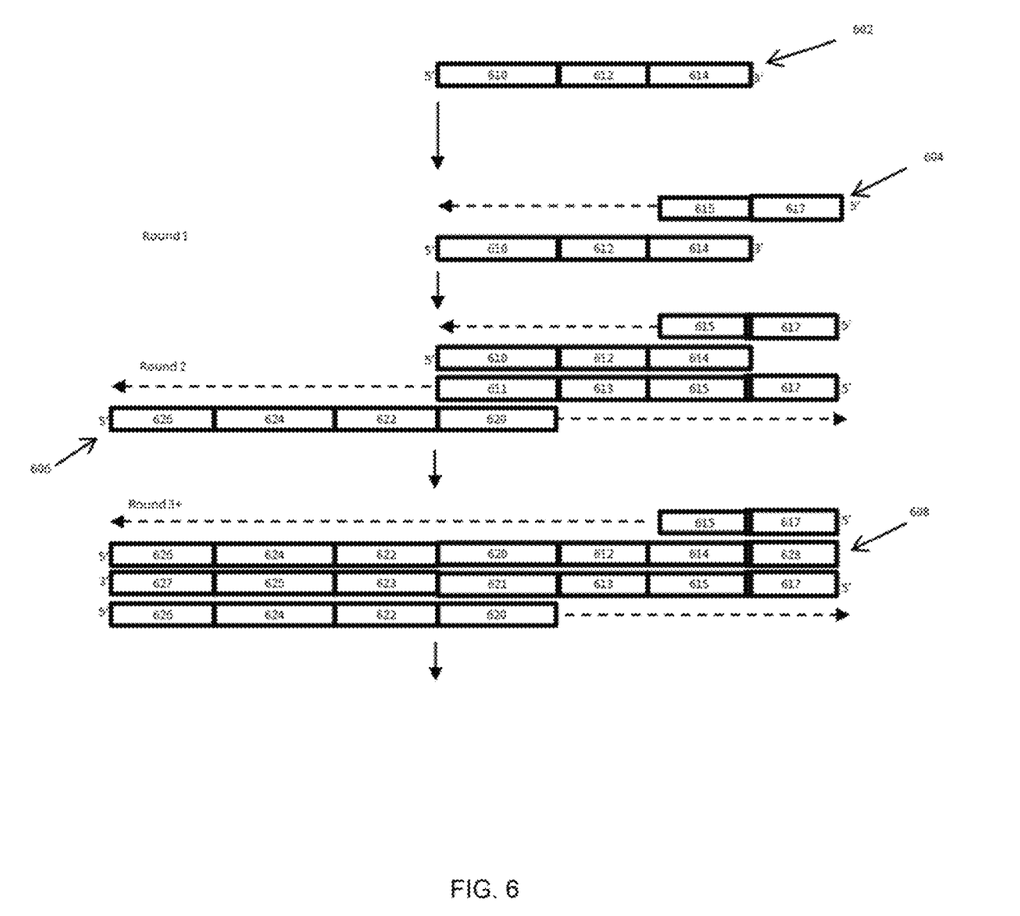
FIG. 6 shows another embodiment of the present methods of attaching an assay identifier to an oligonucleotide having a sample identifier, where the constant regions of the oligonucleotide are not compatible with a desired sequencing platform.

FIG. 6 shows how the present assay methods and compositions can be used to detect contamination in the oligonucleotides when they are surrounded by two constant regions, and neither of those constant regions is compatible with the sequence platform to be used for the assay. Alternatively, this approach can be used to convert adaptors and primers from one sequencing platform so that they can be sequenced on another platform. For example, the oligonucleotides such as adaptors used in an Ion Torrent HaloPlex assay can be assayed using an assay primer containing: Illumina P5, QXT Read1, QC index, IonTorrent Read primers; and an amplification primer containing: Illumina P7 and the reverse complement to the Haloplex dark bases (dark bases are those that do not generate the fluorescence associated with nucleotide incorporation during sequencing). This allows these primers to be assayed for contamination on an Illumina sequencer. This approach can also be used to allow sequencing of oligonucleotides that are not intended for sequencing and do not include amplification regions for sequencing platforms, provided those oligonucleotides comprise a 5' constant region, an unknown region, and a 3' constant region.

In FIG. 6, an oligonucleotide 602 comprises a 5' constant region 610, a sample identifier 612, and a 3' constant region 614. In this embodiment, the constant regions 610, 614 of oligonucleotide 602 are for a first sequencing platform, such as an Ion Torrent sequencing platform, but it is desired to sequence the oligonucleotide 602 on a second sequencing platform, such as an Illumina sequencing platform. For example, the 5' constant region 610 can be an Ion Torrent Adapter A sequence, the sample identifier 612 can be a sample barcode, and the 3' constant region 614 can be dark bases provided to allow for ligation and quality control. The oligonucleotide 602 is amplified using a primer 604 having a priming region 615 complementary to at least a portion of the 3' constant region 614 (that is, complementary to at least a portion of the dark bases). Primer 604 also comprises a region 617 comprising a region corresponding to a standard amplification region for a sequencing platform, for example, an Illumina P7 sequence. The oligonucleotide 602 or complement thereof is amplified with a primer 606 having a priming region 620 complementary to at least a portion of the 5' constant region 610 or its complement 611. The primer 606 also comprises an assay identifier 622 and one or more constant regions (for example an Illumina P5 sequence 626 and an Illumina Read 1 sequence 624). Amplification continues with primer 606 and primer 604 using suitable amplification cycles to provide oligonucleotide amplicons suitable for sequencing on an Illumina sequencing platform. Additional rounds of amplification produce oligonucleotide amplicons 608 comprising one or more constant regions 626, 624, the assay identifier 622, the sequence 620 of the 5' constant region 610 of the initial oligonucleotide 620, the sample identifier 612, the sequence of the 3' constant region 614 and an amplification region 628. The oligonucleotide amplicons 608 are adapted for sequencing on a standard platform for massively parallel sequencing due to the constant regions 626 and/or amplification region 628.

In some embodiments, the presence of a complementary DNA strand (as in the case of an adaptor) may cause problems with detecting contamination or sequence variation, if the complementary adaptor strand contains both of the binding regions for amplification primers. In such situations, both strands will be amplified and any detected contamination/sequence variation could be due to differences in the sequence of the barcode sequence present on the two strands. In many cases, the adaptor design is such that this will not occur.

Example 1

An embodiment of the present methods is employed to determine whether there is sample barcode contamination in a kit having Illumina adapter sequences. As shown in FIG. 1A, an oligonucleotide 102 having a sample identifier 112 is flanked by Illumina Index1 sequence as its 5' constant region 110, and an Illumina P7' sequence as its 3' constant region 114. P7' indicates the complement of P7; likewise, P5' indicates the complement of P5. FIG. 1 illustrates a method for detecting contamination of this oligonucleotide 102 with oligonucleotides having a different sample identifier. Amplification can be performed using a standard DNA polymerase, a P7 primer, and another primer containing P5, a Read 1 Primer sequence, a QC barcode and Index 1 sequence (from 5' to 3', respectively). A high fidelity DNA polymerase can be used to reduce or minimize erroneous contamination detection due to PCR errors.

Figure 2:
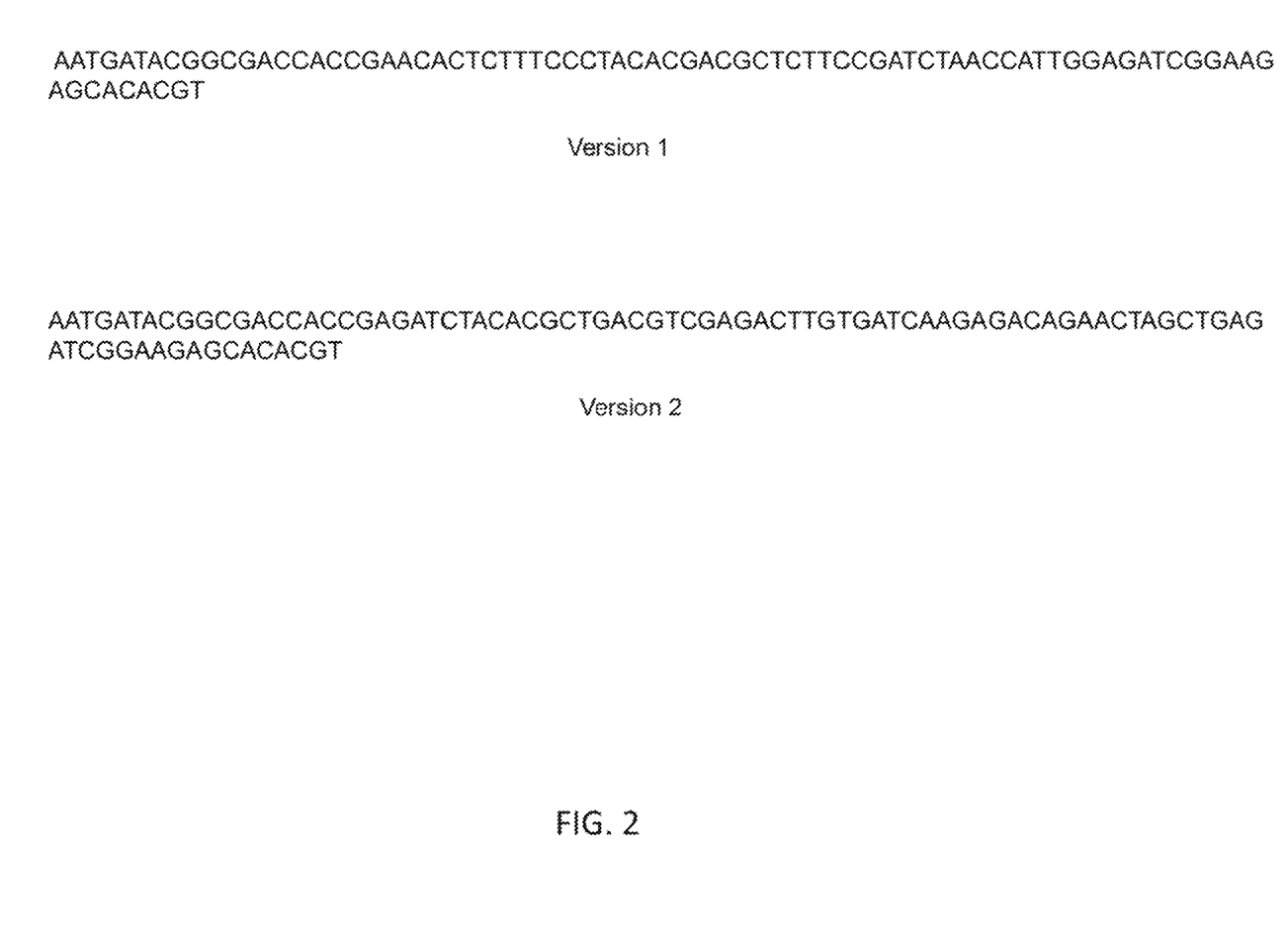
FIG. 2 shows sequence of two different embodiments of assay primers according to the present disclosure. The two embodiments contain many of the same regions, but the 5' constant regions are different. In version 2, there is less overlap between the 5' constant region and the 3' constant region.
Figure 3:
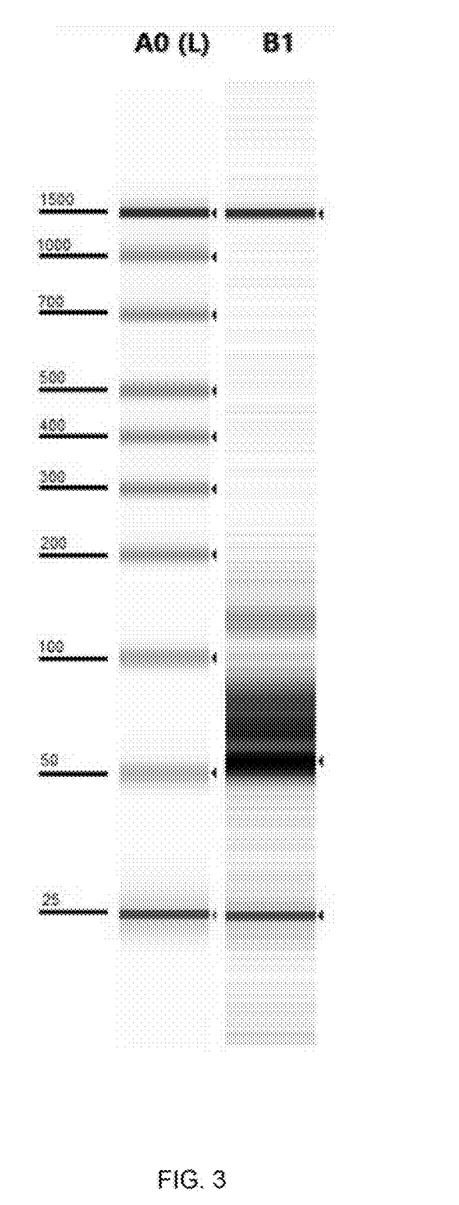
FIG. 3 shows the distribution of amplicon sizes from amplification of an oligonucleotide using the assay primer of the first embodiment in FIG. 2.
Figure 4:
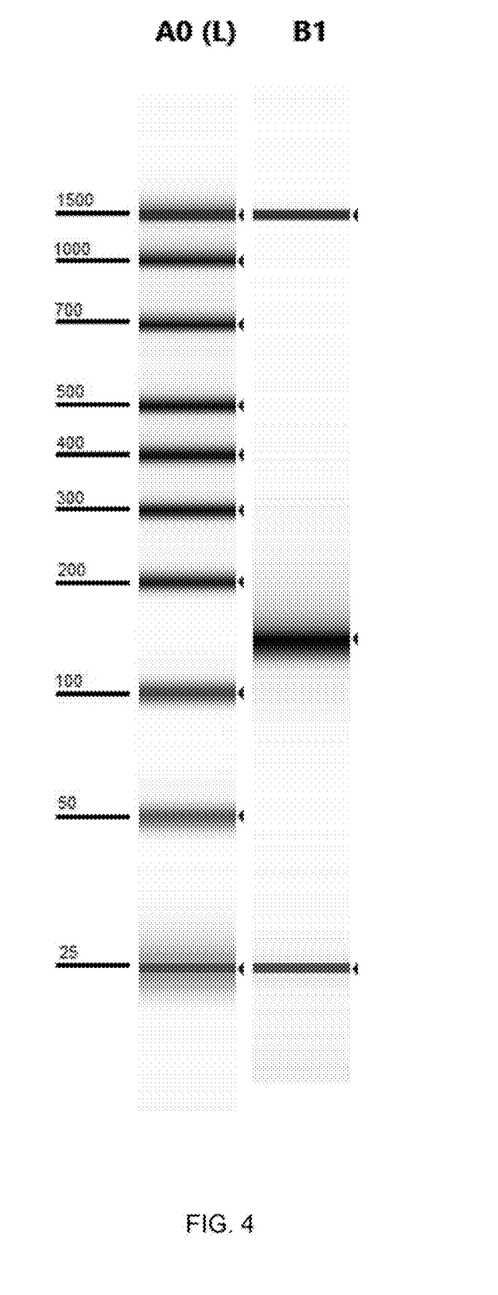
FIG. 4 shows the distribution of amplicon sizes from amplification of an oligonucleotide using the assay primer of the second embodiment in FIG. 2.

Two versions or embodiments of the assay primers were used to develop the assay. The sequences of these two versions are shown in FIG. 2. Initial attempts using version 1 of the assay primer, which contain both the Illumina Read 1 primer and the reverse complement of Illumina Read 2 (Index 1) primer sequence in the assay primer, resulted in a small amount of the expected 130 bp amplicon and a large amount of shorter amplification products (Lane B1 in FIG. 3). These products potentially come from secondary amplification products that are created due to the 13 bp complementarity between the 3' end of Read 1 and the 5' end of Index 1. By changing the sequence of Read 1 from the Illumina sequence to the QXT Read 1 sequence (version 2 of the assay primer), these secondary amplification products were largely eliminated (Lane B1 in FIG. 4).

Example 2

Haloplex and Haloplex HS Kits were tested to see if the oligonucleotide containing the sample barcodes could be amplified in the supplied index solution supplied in the kits. It was found that the oligonucleotides could be cleanly amplified as a strong amplification product was generated when using the assay primer (FIG. 4, lane B1 (supplied index solution)).

Example 3

Assay primers were tested with SureSelect XT and SureSelect XT2 reagent kits, and oligonucleotides were successfully amplified. The present assay primers were also used to test SureSelect XTHS reagent kits, with modifications to the overlap sequence, and oligonucleotides were successfully amplified.

Amplification of these libraries can occur even when the oligonucleotide is modified in a way to prevent elongation, as subsequent rounds after the first two rounds use the synthesized molecule as a template. The amplification method also works in the presence of 5' biotin modifications.

Example 4

A set of 96 or more sample identifiers is provided. The set can be used to add sample identifiers to nucleic acids prior to amplification and/or prior to pooling before sequencing. However, if contamination occurred in one of these sample identifiers during kit assembly or reagent preparation, it could cause the detection of a low allele variant in a sample. To be confident about lack of contamination, it would take a large number of sequencing runs to ensure every sample identifier could be confirmed as having no contamination.

Figure 7:
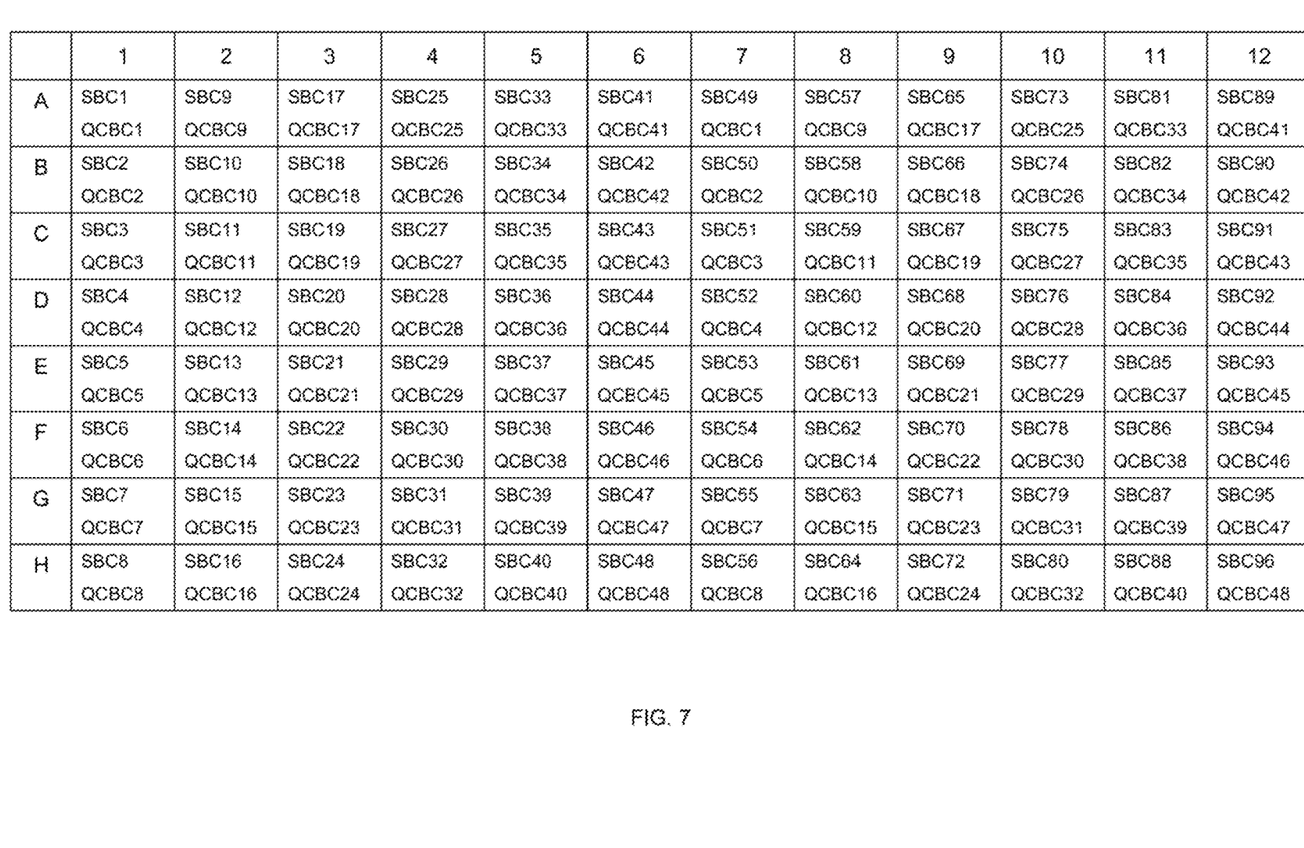
FIG. 7 shows a pooling scheme for detecting contamination of sample identifiers using the present methods and compositions.

The following scheme overcomes this limitation and can be used to determine contamination of sample identifiers (also referred to as sample barcodes or SBCs in this example) and/or assay identifiers (also referred to as QC barcodes or QCBCs in this example). A set of 96 oligonucleotides containing different sample identifiers are split into two groups: Group 1 and Group 2, each containing 48 of the oligonucleotides. Group 1 has SBC1 to SBC48, and Group 2 has SBC49 to SBC96. Each sample identifier in Group 1 is amplified with an assay primer containing one of 48 different assay identifiers (QCBC1 to QCBC48). Each sample identifier in Group 2 is amplified with one of the same 48 assay identifiers that was used in Group 1, such that every assay identifier (QCBC1 through QCBC48) is present in both Groups and in two amplification reactions, and every sample identifier (SBC1 through SBC96) is only present in only one Group and in one amplification reaction. The association of assay identifiers (QCBCs) with sample identifiers (SBCs) according to the scheme is shown in FIG. 7. For illustrative purposes, the SBCs are shown as being arranged in a 96-well plate, though they do not have to be provided or used in well plates.

PCR amplification produces oligonucleotide amplicons having a QCBC and an SBC. In the absence of contamination, each SBC is associated with one QCBC. In other words, when sequenced, the sequence information for each an SBC should have a single QCBC associated with it. FIG. 7 shows the associations that will be produced using this scheme. However, it is desirable to sequence amplicons in pools rather than individually using massively parallel sequencing, thereby reducing time, expense, and effort required for sequencing. Thus, the oligonucleotide amplicons generated in Group 1 are pooled together and sequenced, and the oligonucleotide amplicons from Group 2 are pooled together and sequenced. The sequencing of the pools produces sequence information for the various amplicons included in the pools, and the sequencing information for a given amplicon will have a sample identifier and an assay identifier associated with it.

Sequencing in this manner will allow for the detection of contamination due to sample identifiers or assay identifiers based on the associations identified after analysis of the sequence information. For this analysis, it is helpful to include all the potential sample identifiers (whether then are intended to be present in the pool or not) in the analysis of the sequencing information. If contamination occurs, it can be from the sample identifier or the assay primer. The pattern in which sample identifiers and assay identifiers appear in the two sequencing pools (from Group 1 and Group 2) will determine whether it is sample identifier contamination or assay identifier contamination. The present scheme allows one to determine which is the source of the contamination.

If a sample identifier from Group 2 is observed in Group 1 (for example, if the sequence of SBC66 is found in the sequencing information for Group 1), this indicates contamination of one of the sample barcodes in Group 1, as there are 49 sample identifiers rather than the expected 48. However, this knowledge alone does not indicate which of the sample identifiers in Group 1 was contaminated with SBC66. The specific sample barcode contaminated is determined based on which assay identifier is associated with the contaminating SBC66. If the SBC66 found in the first pool is associated with QCBC10, then SBC10 is the sample identifier that was contaminated with SBC66. Whichever sample identifier in Group 1 has the same assay identifier associated with it as the contaminating sample identifier, that is the sample identifier that is contaminated.

Additionally, the present methods, compositions and kits can also detect contamination within a pool by identifying sample identifiers that are associated with more than one assay identifier and/or by identifying assay identifiers that are associated with more than one sample identifier. If sequence information indicates the presence of amplicons having SBC13 and QCBC13, as well as amplicons having SBC13 and QCBC29 (that is, SBC13 is associated with QCBC13 and with QCBC29), this indicates there is some contamination. However, this knowledge alone does not indicate whether SBC29 was contaminated with SBC13, or whether QCBC13 was contaminated with QCBC29. By identifying whether there is contamination of the same assay identifier in the second pool, one can identify the source of contamination. In the second pool, SBC61 will only be associated with QCBC13 in the absence of contamination. However if SBC61 is also associated with QCBC29, this indicates that QCBC13 was contaminated, since the contamination occurred in both pools. If SBC61 is not associated with QCBC29, then QCBC13 is not contaminated, and SBC29 was the source of contamination in the first pool. The same approach also works for Group 1 sample identifiers present in the Group 2 pool. The present methods provide the ability to differentiate between contamination of a sample identifier and contamination of an assay identifier using two sequencing pools.

The present methods and compositions can also be used to determine sequence variation of random nucleotides found between two constant regions. The assay identifier can act as a standard sample barcode and only one pool of samples would be required, assuming sequencing output is sufficient to detect the level of contamination desired. For instance, this assay can be used to identify low level amount of contamination occurring in sequences where a small variable region exists between two constant regions and may be beneficial for identifying contamination or variation in oligonucleotides used for any intended applications.

The foregoing description of exemplary or preferred embodiments should be taken as illustrating, rather than as limiting, the present invention which is defined by the claims. As will be readily appreciated, numerous variations and combinations of the features set forth above can be utilized without departing from the present invention as set forth in the claims. Such variations are not regarded as a departure from the scope of the invention, and all such variations are intended to be included within the scope of the following claims. All references cited herein are incorporated by reference in their entireties.

We claim:

1. A method for attaching assay identifiers to a set of oligonucleotide samples comprising oligonucleotides, each oligonucleotide comprising a 5' constant region, a sample identifier, and a 3' constant region, the method comprising:
providing each of the oligonucleotide samples of the set in a separate vessel, wherein each vessel comprises only one sample identifier unless one or more of the samples is contaminated;
amplifying the oligonucleotides with an assay primer and a second primer in each vessel, the assay primer comprising one or more constant regions, an assay identifier, and a priming portion that is the same as or complementary to one of the constant regions of the oligonucleotides, wherein each vessel comprises only one assay identifier unless one or more of the assay primers are contaminated;
thereby providing oligonucleotide amplicons comprising an assay identifier and a sample identifier.

2. The method of claim 1, wherein the set of oligonucleotide samples comprises at least 8 samples.

3. The method of claim 1, wherein the oligonucleotide amplicons comprise
a 5' constant region comprising a standard 5' amplification region for a sequencing platform and a sequencing priming region,
an assay identifier,
a middle constant region comprising a sequencing priming region,
a sample identifier, and
a 3' constant region of comprising a standard 3' amplification region for a sequencing platform.

4. The method of claim 3, wherein the standard 5' amplification region comprises a P5 sequence, and the standard 3' amplification region comprises a P7' sequence, or the standard 5' amplification region comprises a P7 sequence, and the standard 3' amplification region comprises a P5' sequence.

5. The method of claim 1, wherein the oligonucleotide amplicons comprise:
a 5' constant region comprising a standard 5' amplification region,
a sample identifier,
a middle constant region,
an assay identifier, and
a 3' constant region comprising a standard 3' amplification region.

6. The method of claim 1, wherein the second primer comprises a 3' region the same or complementary to one of the constant regions of the oligonucleotides, and the second primer further comprises a 5' region comprising a standard amplification region for a sequencing platform, wherein the 5' region of the second primer allows for sequencing on a sequencing platform previous not supported by the sequence of the constant region of the oligonucleotide.

7. The method of claim 1, wherein the oligonucleotides are library molecules.

8. A method for detecting contamination in a set of oligonucleotides for nucleic acid samples, the method comprising:
providing a set of oligonucleotide samples comprising oligonucleotides, each oligonucleotide having a 5' constant region, a sample identifier, and a 3' constant region,
wherein each of the oligonucleotides within a sample has the same sample identifier and each of the samples within the set has a different sample identifier,
unless one or more of the samples is contaminated;
amplifying the oligonucleotides or complements of the oligonucleotides with an assay primer and a second primer, wherein the assay primer is different for each sample, wherein each assay primer comprises a priming portion and an assay identifier, thereby generating a set of oligonucleotide amplicons, each oligonucleotide amplicon comprising one of the assay identifiers, the 5' constant region, one of the sample identifiers, and the 3' constant region;
pooling the oligonucleotide amplicons in one or more pools;
sequencing the one or more pools to determine sequences for at least the sample identifier and the assay identifier of the oligonucleotide amplicons; and
determining whether the sample identifiers in the one or more pools include a contaminating sample identifier.

9. The method of claim 8, further comprising determining whether the assay identifiers in the first pool include a contaminating assay identifier.

10. The method of claim 8, wherein the contaminating sample identifier is determined by one or both of (i) identifying at least one of the sample identifiers that is associated with more than one assay identifier, and (ii) identifying at least one of assay identifiers that is associated with more than one sample identifier.

11. The method of claim 8, wherein the one or more pools comprise a first pool and a second pool;
separately sequencing the first pool and the second pool to determine sequences for at least the sample identifier and the assay identifier of the oligonucleotide amplicons;
determining whether the sample identifiers in the second pool include a contaminating sample identifier.

12. The method of claim 11, further comprising determining whether the assay identifiers in the second pool include a contaminating assay identifier.

13. The method of claim 11, wherein the method further comprises:
identifying a contaminating sample identifier
by determining that the contaminating sample identifier is from a second pool.

14. The method of claim 11, wherein the method further comprises:
identifying a contaminating sample identifier by determining that the second pool does not include a contaminating assay identifier.

15. The method of claim 11, wherein the method further comprises:

identifying a contaminating assay identifier by determining that the second pool includes a contaminating assay identifier.

16. The method of claim 8, wherein the set of oligonucleotides comprises at least 8 oligonucleotides.

17. The method of claim 8, further comprising one or both of:

grouping sequences of the oligonucleotide amplicons according to the assay identifiers to form assay groups, and determining if there is more than one sample identifier sequence in each of the assay groups; and grouping sequences of the oligonucleotide amplicons according to the sample identifiers to form sample groups, and determining if there is more than one assay identifier sequence in each of the sample groups.

18. The method of claim 8, comprising determining a mismatch between at least one of the assay identifiers and at least one of the sample identifiers.

\* \* \* \* \*

SEQUENCE LISTING

<160> NUMBER OF SEQ ID NOS: 8

<210> SEQ ID NO 1
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 1
aatgatacgg cgaccaccga                                            20

<210> SEQ ID NO 2
<211> LENGTH: 24

<212> TYPE: DNA
<213> ORGANISM: Artificial Sequence
<220> FEATURE:
<223> OTHER INFORMATION: Synthetic Sequence

<400> SEQUENCE: 2
caagcagaag acggcatacg agat        24

<210> SEQ ID NO 3
<211> LENGTH: 33
<212> TYPE: DNA
<213> ORGANISM: Artificial Sequence
<220> FEATURE:
<223> OTHER INFORMATION: Synthetic Sequence

<400> SEQUENCE: 3
acactctttc cctacacgac gctcttccga tct        33

<210> SEQ ID NO 4
<211> LENGTH: 33
<212> TYPE: DNA
<213> ORGANISM: Artificial Sequence
<220> FEATURE:
<223> OTHER INFORMATION: Synthetic Sequence

<400> SEQUENCE: 4
gatcggaaga gcacacgtct gaactccagt cac        33

<210> SEQ ID NO 5
<211> LENGTH: 34
<212> TYPE: DNA
<213> ORGANISM: Artificial Sequence
<220> FEATURE:
<223> OTHER INFORMATION: Synthetic Sequence

<400> SEQUENCE: 5
gtgactggag ttcagacgtg tgctcttccg atct        34

<210> SEQ ID NO 6
<211> LENGTH: 33
<212> TYPE: DNA
<213> ORGANISM: Artificial Sequence
<220> FEATURE:
<223> OTHER INFORMATION: Synthetic Sequence

<400> SEQUENCE: 6
agatcggaag agcgtcgtgt agggaaagag tgt        33

<210> SEQ ID NO 7
<211> LENGTH: 30
<212> TYPE: DNA
<213> ORGANISM: Artificial Sequence
<220> FEATURE:
<223> OTHER INFORMATION: Synthetic Sequence

<400> SEQUENCE: 7
ccatctcatc cctgcgtgtc tccgactcag        30

<210> SEQ ID NO 8
<211> LENGTH: 23
<212> TYPE: DNA
<213> ORGANISM: Artificial Sequence
<220> FEATURE:

```
<223> OTHER INFORMATION: Synthetic Sequence

<400> SEQUENCE: 8
cctctctatg ggcagtcggt gat                                           23
```

UNITED STATES PATENT AND TRADEMARK OFFICE
CERTIFICATE OF CORRECTION

PATENT NO. : 10,633,651 B2
APPLICATION NO. : 15/645085
DATED : April 28, 2020
INVENTOR(S) : Katie Leigh Zobeck et al.

Page 1 of 1

It is certified that error appears in the above-identified patent and that said Letters Patent is hereby corrected as shown below:

In the Specification

In Column 9, Line 41, delete "lumina" and insert -- Illumina --, therefor.

In Column 9, Line 45, delete "Illuminna" and insert -- Illumina --, therefor.

In Column 10, Line 10, delete "con irises" and insert -- comprises --, therefor.

Signed and Sealed this
Thirtieth Day of June, 2020

Andrei Iancu
*Director of the United States Patent and Trademark Office*